United States Patent [19]
Lentini et al.

[11] Patent Number: 5,514,367
[45] Date of Patent: May 7, 1996

[54] SKIN TANNING COMPOSITIONS AND METHODS FOR THEIR PREPARATION AND USE

[75] Inventors: Peter J. Lentini, Glen Oaks, N.Y.; Julius R. Zecchino, Closter, N.J.

[73] Assignee: Estee Lauder, Inc., New York, N.Y.

[21] Appl. No.: 203,148

[22] Filed: Feb. 28, 1994

[51] Int. Cl.⁶ .............................. A61K 7/42; A61K 7/02; A61K 7/035; A61K 9/10
[52] U.S. Cl. .............................. 424/59; 424/63; 424/69; 514/938
[58] Field of Search .......................... 424/59, 63

[56] References Cited

U.S. PATENT DOCUMENTS

| | | | |
|---|---|---|---|
| 2,948,657 | 8/1960 | Siccama et al. | 424/59 |
| 4,383,992 | 5/1983 | Lipari | 424/238 |
| 5,232,688 | 8/1993 | Ziegler et al. | 424/59 |
| 5,318,774 | 6/1994 | Alban et al. | 514/938 |

FOREIGN PATENT DOCUMENTS

| | | | |
|---|---|---|---|
| 0246090A2 | 5/1987 | European Pat. Off. | 424/20 |
| 0547864A1 | 12/1992 | European Pat. Off. | 424/63 |

OTHER PUBLICATIONS

Citernesi et al., "Ciclodestrine in Dermocosmesi Funzionale", *Cosmetics & Toiletries Ed. It.*, 13(3): 15, 17–26 (1992) with partial translation.

Zanotti, F., "I complessi di ciclodestrina in cosmesi", *Cosmetics & Toiletries Ed. It.*, 11(6): 17, 20–21, 25, 28–29, 32 (1990) with English abstract.

*Primary Examiner*—Dale R. Ore
*Attorney, Agent, or Firm*—Pennie & Edmonds

[57] ABSTRACT

The present invention provides novel cosmetic compositions for artificially tanning the skin utilizing skin tanning agents and cyclodextrins. The compositions are exceptionally stable and reduce the odor associated with the reaction between skin tanning agents such as dihydroxyacetone and the skin.

28 Claims, No Drawings

SKIN TANNING COMPOSITIONS AND METHODS FOR THEIR PREPARATION AND USE

FIELD OF THE INVENTION

This invention relates to cosmetic compositions for providing an artificial tan to skin and methods for their preparation and use. More specifically, the invention relates to skin tanning compositions which comprise a skin tanning agent and one or more cyclodextrins in a cosmetically acceptable carrier.

BACKGROUND OF THE INVENTION

Many individuals have a skin complexion which does not tan readily on exposure to sunlight. Others achieve a tan only with great discomfort and possibly adverse effects to the skin due to exposure to the sun's rays, e.g., sunburn. Yet attainment of a tan by many individuals is highly desired for cosmetic and other reasons, especially if this can be accomplished without the usual exposure to the sun, i.e., through skin tanning agents.

In other instances, individuals who tan with difficulty may desire to extend the life of a naturally acquired tan without re-exposure to the sun. Also, a skin tan may be desired when weather conditions do not permit the sun exposure necessary to acquire a tan.

Acquisition of a natural tan by exposure to the sun, however, may be almost impossible for those very light skinned persons who tend to burn rather than tan. In addition, the deleterious effects of excessive exposure to sunlight are becoming more generally recognized.

It is known in the art that an artificial tan can be achieved by applying skin tanning agents to the human skin in a suitable vehicle or base. Examples of known skin tanning agents include hydroxyaldehydes such as dihydroxyacetone; see U.S. Pat. Nos. 2,949,403 and 5,232,688. Also known as skin tanning agents are imidazole and various imidazole derivatives, such as 4-(hydroxymethylimidazole); see U.S. Pat. No. 5,252,322.

U.S. Pat. No. 2,949,403 discloses compositions of and methods of using dihydroxyacetone as a tanning agent for the human epidermis. It has been reported that dihydroxyacetone reacts with skin proteins and amino acids to elicit its skin coloring effect. Since the 1960's, several compositions using dihydroxyacetone as an active ingredient have been reported. These compositions include a topical composition containing dihydroxyacetone and various dyes such as catch powder, dogwood powder and walnut powder (the dyes are employed to offset the undesirable orange cast or hue which results from the use of dihydroxyacetone on fair skinned humans, see U.S. Pat. No. 4,708,865). These also include compositions containing dihydroxyacetone and sunscreen compounds such as octyl dimethyl PABA (e.g., U.S. Pat. Nos. 4,434,154 and 3,177,120).

Further, dihydroxyacetone has been formulated into oil-in-water emulsions, into preparations containing up to 50% alcohol which tends to dry the skin, and into "creamy bases" such as are found in hand and face lotions and creams.

U.S. Pat. No. 5,232,688 discloses compositions for self-tanning of skin which include an alpha-hydroxy substituted ketone or aldehyde such as dihydroxyacetone, a polyacrylamide and a pharmaceutically acceptable carrier.

While dihydroxyacetone has been widely employed as a skin tanning agent, commercial preparations containing dihydroxyacetone suffer from a number of drawbacks. A particular disadvantage is the physical and chemical degradation of dihydroxyacetone containing preparations over extended periods of time, for example during warehouse storage or consumer usage. Such degradation leads to discoloration, the development of unpleasant odors, and an overall loss of stability and skin-tanning efficiency. A further disadvantage of such preparations is the development of aesthetically unacceptable odors following the application of such preparations to the skin. This is thought to occur as a result of the reaction between dihydroxyacetone and the skin which results in skin tanning.

Other skin tanning agents include imidazoles, for example, see U.S. Pat. No. 5,252,322 which discloses skin tanning compositions containing imidazoles. U.S. Pat. No. 5,252,322 discloses that such compounds are believed to function by stimulating the natural processes in the skin which result in a tan. This patent further discloses several limitations to the use of imidazoles in skin tanning compositions, such as the limited solubility of such compounds in aqueous or alcoholic environments, and the possibility of skin irritation which may result when such compounds are used above certain concentrations.

Cyclodextrins have been used to encapsulate specific ingredients in cosmetic compositions; see U.S. Pat. Nos. 4,383,992, and 4,847,074. Lipari et al. in U.S. Pat. No. 4,383,992 disclose water-soluble steroid compounds formed by complexing beta-cyclodextrin with asteroid compound. Lipari et al. further disclose that various steroid compounds, including corticosteroids, androgens, anabolic steroids, estrogens and progestagens, can be used to form inclusion compounds with beta-cyclodextrin. Hatae et al. in U.S. Pat. No. 4,847,074 disclose a whitening cosmetic comprising kojic acid and cyclodextrin. Hatae et al. further disclose that such compositions have an improved stability against coloring as well as an enhanced whitening effect.

There is clearly a need for skin tanning compositions which can provide an artificial tan to the skin in a safe and nonirritating manner. There is also clearly a need for skin tanning compositions which are stable over extended periods of time, and are aesthetically pleasing to use. Further, there is a need for skin tanning compositions which efficiently tan the skin without causing unpleasant odors in the process.

It is therefore an object of the present invention to provide skin tanning compositions which are stable against physical and chemical degradation over time. It is another object of this invention to provide skin tanning compositions which color the skin without the development of unpleasant odors or skin irritation. It is a further object of this invention to provide a method for the preparation of such compositions. It is a still further object of this invention to provide a method for the use of such compositions in providing an artificial tan to human skin.

These and other objects of the present invention are achieved by incorporating effective amounts of one or more cyclodextrins and one or more skin tanning agents into cosmetic compositions. We believe this invention constitutes the first use of a cyclodextrin and a skin tanning agent such as dihydroxyacetone in a skin tanning composition.

SUMMARY OF THE INVENTION

In accordance with the present invention there are provided skin tanning compositions comprising:

(a) an effective amount of a skin tanning agent;

(b) at least one cyclodextrin; and (c) a cosmetically acceptable carrier.

It is also acceptable to use one or more skin tanning agents with one or more cyclodextrins. Various optional ingredients can also be used, such as penetration enhancers, sugars, preservatives, emollients, antibacterials, pigments, dyes, humectants, stabilizers, antioxidants, vitamins, propellants, emulsifiers, emulsion stabilizers, antioxidants, sunscreen, dermatologically active agents, and fragrances.

In another embodiment, the present invention provides a skin tanning composition comprising:

(a) an effective amount of dihydroxyacetone;

(b) at least one cyclodextrin; and (c) a cosmetically acceptable carrier.

The present invention also relates to a method for preparing such compositions, the method comprising the steps of:

(a) mixing a skin tanning agent with a cosmetically acceptable carrier; and (b) mixing a cyclodextrin with said cosmetically acceptable carrier.

It is to be understood that step (b) set forth above may be conducted prior to the skin tanning agent being dissolved with the cosmetically acceptable carrier, or during or after the dissolution step. It is to be further understood that the term "mixing" and "mixture" in this application are used in the broad sense of the words, with the term "mixture," including, without limitation, blends, solutions and suspensions, etc.

The compositions of the present invention are chemically and physically stable, nonirritating and aesthetically pleasing cosmetics. In addition, the compositions of this invention do not discolor or develop disagreeable odors over time. It has unexpectedly been found that the compositions of the present invention do not develop aesthetically unacceptable odors following application to the skin. The compositions are particularly useful for providing an artificial tan to skin. The present invention also encompasses methods of using the novel skin tanning compositions of the present invention to artificially tan the skin.

DETAILED DESCRIPTION OF THE INVENTION

As mentioned hereinabove, the present invention provides skin tanning compositions comprising: (a) an effective amount of a skin tanning agent; (b) at least one cyclodextrin; and (c) a cosmetically acceptable carrier.

In another embodiment, the present invention provides a skin tanning composition comprising:

(a) an effective amount of dihydroxyacetone;

(b) at least one cyclodextrin; and (c) a cosmetically acceptable carrier.

The skin tanning compositions of the present invention are cosmetic compositions suitable for topical application to animals, particularly humans. The cosmetic compositions are particularly suitable for topical applications in the form of, including but not limited to, sprays, mists, creams, lotions, gels, powders, masks, emulsions and solutions.

As described above, the main components of these skin tanning compositions are a skin tanning agent, and at least one cyclodextrin in a cosmetically acceptable carrier. Clearly, various optional ingredients, including but not limited to penetration enhancers, sugars, fragrances, preservatives, emulsifiers, antibacterials, pigments, dyes, humectants, propellants, emollients, stabilizers, as well as other classes of materials whose presence may be cosmetically, medicinally or otherwise desirable, can also be used in these compositions. It is essential, however, to have at least one skin tanning agent and one or more cyclodextrins or combinations thereof in a cosmetically acceptable carrier to achieve all the benefits that the compositions of the present invention can provide.

As used herein and in the relevant art, a skin tanning agent is a material that is capable of coloring the skin; in particular, a material capable of darkening the skin so that it resembles the darkening effect achieved by exposure of one's skin to the sun's rays (i.e., a natural tan). Several skin tanning agents are known in the cosmetic art. Any of these can be used within the present invention. For example, alpha-hydroxy aldehydes may be used, including but not limited to, dihydroxyacetone and derivatives thereof, similarly imidazole and imidazole derivatives can be used. Dihydroxyacetone is preferred. In one embodiment of the present invention, an effective amount of a skin tanning agent is from about 0.1 to about 20 percent of the total weight of the composition; in a preferred embodiment, an effective amount of a skin tanning agent is from about 2 to about 15 percent; and in a most preferred embodiment an effective amount of a skin tanning agent is from about 5 to about 10 percent.

In a preferred embodiment of the present invention, the skin tanning agent is dihydroxyacetone. Dihydroxyacetone is available from E Merck and Company (Dharmstadtt). An effective amount of dihydroxyacetone is from about 0.1 to about 20 percent of the total composition; in a preferred embodiment, an effective amount of dihydroxyacetone is from about 2 to about 15 percent; and in a most preferred embodiment an effective amount of dihydroxyacetone is from about 5 to about 10 percent.

Cyclodextrins constitute a family of natural cyclic oligosaccharides which are known to be capable of forming inclusion complexes with a variety of materials; see "Inclusion Compounds" (J. L. Atwood et al., eds., Academic Press Inc., Orlando, Fla., 1984). Cyclodextrins of varying ring sizes are known; those comprising six, seven or eight glucose residues are commonly referred to as alpha-cyclodextrins, beta-cyclodextrins and gamma-cyclodextrins, respectively. Cyclodextrin, cycloamylose, cycloglucans are naturally occurring clathrates obtained from the action of Bacillus Macerans amylase on starch to form homogeneous cyclic alpha-(1–4) linked D-glucopyranose units. We are not aware of any use of a skin tanning agent such as dihydroxyacetone in conjunction with a cyclodextrin in a skin tanning composition, prior to this invention.

It has unexpectedly been found that when an effective amount of at least one cyclodextrin is added to a cosmetic composition containing a skin tanning agent such as dihydroxyacetone, that the composition is rendered more stable, e.g., has a longer storage life; the composition has a reduced odor under storage and use; and the odor caused by the reaction of dihydroxyacetone with the skin is dramatically reduced.

One or more cyclodextrins can be used either alone or in combination in the present compositions. These cyclodextrins are selected from the group consisting of α-cyclodextrin, β-cyclodextrin, γ-cyclodextrin, δ-cyclodextrin and cationized cyclodextrins. The cyclodextrins used within the present invention can be purchased from American Maize. The preferred cyclodextrins are alpha-gramma-cyclodextrin. The most preferred is gamma-cyclodextrin (Cavitron 8®).

In one embodiment of the present invention, an effective amount of cyclodextrin is from about 0.1 to about 10 percent of the total weight of the composition; in a preferred embodiment an effective amount of cyclodextrin is from about 1.0 to about 8 percent; and in a most preferred embodiment an effective amount of cyclodextrin is from about 1.5 to about 6 percent. The weight percents constitute the total weight of cyclodextrin whether one or a combination of more than one cyclodextrin is used.

The cosmetic carrier as used herein includes any vehicle or base which is capable of delivering the skin tanning agent and cyclodextrin to the skin. The cosmetically acceptable carrier can be in the form of, including but not limited to, a spray, mist, cream, lotion, gel, powder, mask, solution or emulsion. The cosmetically acceptable carrier of the present invention is preferably an emulsion. The preferred emulsion is a water-in-silicone emulsion. The water-in-silicone emulsions are comprised of a mixture of hydrocarbons and silicons in water; for example, a mixture of hydrocarbons, volatile silicones and alkylated derivatives of polymeric silicones (hydrogenated polyisobutene, cyclomethicone and cetyl dimethicone). It has also been found that sodium chloride is useful as a stabilizing agent in the cosmetic carriers of this invention. As used herein, the cosmetically acceptable carrier can include optional ingredients known to those skilled in the art, including but not limited to, preservatives, fragrances, emollients, anti-inflammatories, antibacterials, emulsifiers and other suitable ingredients found in the CTFA International Cosmetics Ingredients Dictionary (The Cosmetic, Toiletry and Fragrance Association, Washington, D.C. 1991).

The skin tanning compositions of the present invention, particularly those utilizing dihydroxyacetone, may also contain one or more penetration enhancers. An acceptable amount of penetration enhancers in the composition is from about 0.5 to about 25 percent of the composition. As used herein, a penetration enhancer is a material capable of aiding the penetration of the skin tanning agent into the skin so that a deeper, longer lasting artificial tan can be achieved. Examples of penetration enhancers include, but are not limited to, dimethyl isosorbide and diethyl-glycol-monoethylether.

Further, it has been found that the skin tanning compositions of the present invention achieve better artificial tanning results when sugars are used in the composition. As used herein, the term "sugar" includes monosaccharides, disaccharides and polysaccharides. Examples of sugars useful in the compositions of the present invention include, but are not limited to, glucose, xylose, fructose, reose, ribose, pentose, arabinose, allose, tallose, altrose, mannose, galactose, lactose, sucrose, erythrose, glyceraldehyde and combinations thereof. Sucrose, glucose and fructose are preferred. An acceptable amount of sugar in the composition is from about 0.5 to about 20 percent of the composition.

Various optional ingredients may be included in the compositions of the present invention, these include but are not limited to perfumes, preservatives, emollients, antiseptics, antibacterials, stabilizers, antioxidants, vitamins, pigments, dyes, humectants, propellants, as well as other classes of materials whose presence may be cosmetically, medicinally or otherwise desirable. Common examples can be found in the CTFA International Cosmetic Ingredient Dictionary 4th Edition, The Cosmetic, Toiletry, and Fragrance Association, Inc., Washington, D.C., 1991. Common examples of such ingredients are provided below by way of example and not limitation.

Optional ingredients include polyoxyethylene ethers such as PPG-12-buteth-16 (UCON 50 HB 660), PPG-3-buteth 5, PPG-5-buteth 7, PPG-7-buteth 10, PPG-9-buteth 12, PPG-12-buteth 16, PPG-15-buteth 20, PPG-20-buteth 30, PPG-28-buteth 35, PPG-33-buteth 45, PEG-4, PEG-6, PEG-8, PEG-10, PEG-12, PEG-32, or suitable ingredients which provide emolliency; hydrolyzed wheat protein/wheat oligosaccharides such as Cropeptide W®, hydrolyzed corn protein, hydrolyzed corn starch, hydrolyzed wheat gluten, hydrolyzed yeast protein, hydrolyzed vegetable protein, hydrolyzed soy protein, hydrolyzed rice protein, hydrolyzed potato protein, which are suitable for moisturization; polyethylene glycol esters such as PEG-14 Laurate, PEG-15 Laurate, PEG-20 Laurate, PEG-32 Laurate, PEG-75 Laurate, PEG-150 Laurate or other surfactants which are used for fragrance solubilization; glycereth-7-triacetate (Dermol GL-7A, Alzo), glycerin, glycereth 5 lactate, glycereth 7 diisonanoate which are used for moisturization, emolliency and to help solubilize fragrance; PEG-40 Castor Oil (Surfactol 365, CasChem), PEG 45 castor oil, PEG 50 castor oil, PEG 60 castor oil, PEG 100 castor oil which are surfactants to help solubilize fragrance and also provide emolliency and moisturization; preservatives such as methyldibromo-glutaronitrile/phenoxyethanol/polyquaternium-7 (Euxyl K-400, Calgon) methyl paraben, imidazolidinyl urea benzalkonium chloride, diazolidinyl urea, benzethonium chloride, sodium benzoate and sorbic acid; sunscreens such as octyldimethyl PABA, benzophenone-4, DEA-methoxycinnamate, 2-phenyl-benzimidazole-5-sulphonic acid and TEA salicylate; and finally fragrances.

The skin tanning compositions of the present invention are suitable for use on the human epidermis (skin). In order to achieve an acceptable artificial tan, a person who desires such an artificial tan evenly applies an effective amount of the skin tanning composition on the desired areas of the skin. The compositions will imbue an artificial tan on the skin while reducing the unpleasant odor normally associated with the reaction between the skin tanning agent and the skin.

The compositions of the present invention can be stored at room temperature between uses without significant or rapid degradation of the active components which is known to occur with certain skin tanning compositions.

The following examples are given to illustrate the present invention. Because these examples are given for illustrative purposes only, the invention should not be inferred to be limited to these examples.

EXAMPLES

EXAMPLE 1

| SELF ACTION TANNING SPRAY | |
|---|---|
| INGREDIENT NAME | PERCENT |
| DEIONIZED WATER | 62.5 |
| DIHYDROXYACETONE | 5.0 |
| 1,3-BUTYLENE GLYCOL | 5.0 |
| METHOCEL K4M PREMIUM (2% aq)* | 10.0 |

-continued

SELF ACTION TANNING SPRAY

| INGREDIENT NAME | PERCENT |
| --- | --- |
| ARLASOLVE DMI (dimethyl isosorbide) | 5.0 |
| TRANSCUTOL (ethoxydiglycol) | 5.0 |
| SUCROSE | 2.0 |
| GLUCOSE | 2.0 |
| FRUCTOSE | 2.0 |
| CAVITRON 8 (GAMMA CYCLODEXTRIN) | 1.5 |

*Hydroxypropyl methylcellulose

EXAMPLE 2

SELF ACTION TANNING THIN GEL

| INGREDIENT NAME | PERCENT |
| --- | --- |
| DEIONIZED WATER | 72.5 |
| DIHYDROXYACETONE | 5.0 |
| 1,3-BUTYLENE GLYCOL | 5.0 |
| ARLASOLVE DMI (dimethyl isosorbide) | 5.0 |
| TRANSCUTOL (ethoxydiglycol) | 5.0 |
| SUCROSE | 2.0 |
| GLUCOSE | 2.0 |
| FRUCTOSE | 2.0 |
| CAVITRON 8 (GAMMA CYCLODEXTRIN) | 1.5 |

EXAMPLE 3

SELF ACTION TANNING LOTION

| INGREDIENT NAME | PERCENT |
| --- | --- |
| DEIONIZED WATER | 58.5 |
| DIHYDROXYACETONE | 5.0 |
| 1,3-BUTYLENE GLYCOL | 5.0 |
| ARLASOLVE DMI (dimethyl isosorbide) | 5.0 |
| TRANSCUTOL (ethoxydiglycol) | 5.0 |
| ARLACEL 165* | 4.0 |
| LEXOL GT-865 (caprylic/capric triglyceride) | 10.0 |
| SUCROSE | 2.0 |
| GLUCOSE | 2.0 |
| FRUCTOSE | 2.0 |
| CAVITRON 8 (GAMMA CYCLODEXTRIN) | 1.5 |

*Glyceryl stearate and PEG-100 stearate (ICI Americas)

EXAMPLE 4

SELF ACTION TANNING GEL/CREAM

| INGREDIENT NAME | PERCENT |
| --- | --- |
| DEIONIZED WATER | 50.5 |
| DIHYDROXYACETONE | 5.0 |
| 1,3-BUTYLENE GLYCOL | 5.0 |
| ARLASOLVE DMI (dimethyl isosorbide) | 5.0 |
| TRANSCUTOL (ethoxydiglycol) | 5.0 |
| ABIL EM-90* | 2.0 |
| DOW CORNING 344 FLUID (cyclomethicone) | 20.0 |
| SUCROSE | 2.0 |
| GLUCOSE | 2.0 |
| FRUCTOSE | 2.0 |
| CAVITRON 8 (GAMMA CYCLODEXTRIN) | 1.5 |

*Cetyl dimethicone copolyol (Goldschmidt)

EXAMPLE 5

PREPARATION OF THE SKIN TANNING COMPOSITIONS OF EXAMPLES 1–4

The above-listed formulae are preferably made by combining water-soluble materials separately from the oils and homogenizing at room temperature, except for the lotion of Example 3, which is made by melting the oil soluble materials at about 55° C. and combining that with the water-soluble materials at about 40° C. and homogenizing, then cooling to room temperature.

It may be apparent to those skilled in the art that modifications and variations of the present invention are possible in light of the above disclosure. It is understood that such modifications are within the spirit and scope of the invention, which is limited and defined only by the appended claims.

What is claimed is:

1. A skin tanning composition which comprises:

(a) an effective amount of a skin tanning agent;

(b) an effective amount of at least one cyclodextrin; and (c) a cosmetically acceptable carrier.

2. The composition of claim 1, wherein the cyclodextrin is selected from the group consisting of alpha-cyclodextrin, beta-cyclodextrin, gamma-cyclodextrin, and delta-cyclodextrin or combinations thereof.

3. The composition of claim 2, wherein the cyclodextrin is gamma-cyclodextrin.

4. The composition of claim 1, wherein the cosmetically acceptable carrier is an emulsion.

5. The composition of claim 4, wherein the emulsion is a water-in-silicone emulsion.

6. The composition of claim 1, further comprising a penetration enhancer.

7. The composition of claim 6, wherein the penetration enhancer is transcutol.

8. The composition of claim 6, wherein the penetration enhancer is dimethyl isosorbide.

9. The composition of claim 1, further comprising a sugar selected from the group consisting of sucrose, glucose and fructose.

10. A skin tanning composition which comprises:

(a) from about 0.1 to about 20 percent of a skin tanning agent;

(b) from about 1 to about 10 percent of at least one cyclodextrin;

(c) from about 1 to about 10 percent of a penetration enhancer;

(d) from about 6 to about 10 percent of a sugar selected from the group consisting of sucrose, glucose and fructose; and (e) a cosmetically acceptable carrier.

11. A skin tanning composition which comprises:

(a) an effective amount of dihydroxyacetone;

(b) an effective amount of at least one cyclodextrin; and (c) a cosmetically acceptable carrier.

12. The composition of claim 11, wherein the cyclodextrin is selected from the group consisting of alpha-cyclodextrin, beta-cyclodextrin, gamma-cyclodextrin, delta-cyclodextrin and combinations thereof.

13. The composition of claim 12, wherein the cyclodextrin is gamma-cyclodextrin.

14. The composition of claim 13, wherein the cosmetically acceptable carrier is an emulsion.

15. The composition of claim 14, wherein the emulsion is a water-in-silicone emulsion.

16. The composition of claim 15, further comprising a penetration enhancer.

17. The composition of claim 16, wherein the penetration enhancer is transcutol.

18. The composition of claim 16, wherein the penetration enhancer is dimethyl isosorbide.

19. The composition of claim 11, further comprising a sugar selected from the group consisting of sucrose, glucose and fructose.

20. A skin tanning composition which comprises:
    (a) from about 0.1 to about 20 percent of a dihydroxyacetone;
    (b) from about 1 to about 10 percent of at least one cyclodextrin; and
    (c) a cosmetically acceptable carrier.

21. A skin tanning composition which comprises:
    (a) from about 0.1 to about 20 percent of dihydroxyacetone;
    (b) from about 1 to about 10 percent of at least one cyclodextrin;
    (c) from about 0.5 to about 50 percent of a penetration enhancer;
    (d) from about 0.5 to about 20 percent of at least one sugar; and
    (e) a cosmetically acceptable carrier.

22. The composition of claim 21, wherein the amount of dihydroxyacetone is from about 5 to about 10 percent.

23. The composition of claim 21 wherein the amount of cyclodextrin is from about 1.5 to about 6 percent.

24. The composition of claim 21 wherein the cosmetically acceptable carrier is an emulsion.

25. The composition of claim 24 wherein the emulsion is a water-in-silicone emulsion.

26. A method for the preparation of a skin tanning composition comprising dihydroxyacetone, a cyclodextrin and a cosmetically acceptable carrier, which comprises:
    (a) combining the dihydroxyacetone with the cosmetically acceptable carrier; and
    (b) combining the cyclodextrin with the cosmetically acceptable carrier at a temperature of no greater than 35° C.

27. A skin tanning composition prepared according to the method of claim 26.

28. A method of providing an artificial tan to human skin which comprises applying the composition of claims 1, 10, 11, 20, 21 or 27 to the skin.

* * * * *